United States Patent [19]

Bronner

[11] 4,108,309

[45] Aug. 22, 1978

[54] CONTRACEPTIVE CONTAINING DEVICE

[75] Inventor: Emanuel H. Bronner, Escondido, Calif.

[73] Assignee: All One God Faith, Inc., Escondido, Calif.

[21] Appl. No.: 779,489

[22] Filed: Mar. 21, 1977

Related U.S. Application Data

[63] Continuation-in-part of Ser. No. 732,800, Oct. 13, 1976, Pat. No. 4,027,670.

[51] Int. Cl.$^2$ ............... A61J 3/08; B65D 77/38
[52] U.S. Cl. ................. 206/528; 206/466; 206/531; 206/532; 206/620; 128/271; 128/272; 424/317; 424/DIG. 14
[58] Field of Search ........... 128/260, 261, 272, 272.3, 128/270, 271; 206/216, 229, 364, 484, 489, 498, 438, 528, 828, 570, 535, 536, 306, 472, 473, 529, 538, 601, 604, 620, 219, 363; 424/DIG. 14, 28, 317

[56] References Cited

U.S. PATENT DOCUMENTS

| | | | |
|---|---|---|---|
| 1,216,094 | 2/1917 | Duganne | 206/820 |
| 2,012,531 | 8/1935 | Goldine | 128/261 X |
| 2,149,240 | 2/1939 | Crossley | 424/317 |
| 2,185,536 | 1/1940 | Borland et al. | 128/261 |
| 2,658,613 | 11/1953 | Volckening | 206/620 |
| 2,687,130 | 8/1954 | Cohen | 128/272 |
| 2,687,730 | 8/1954 | Hein, Jr. | 128/272 |
| 2,777,796 | 1/1957 | Elias | 424/28 |
| 2,783,877 | 3/1957 | Volckening | 206/474 |
| 2,864,368 | 12/1958 | Senger | 128/261 |
| 2,902,146 | 9/1959 | Doherty | 206/438 |
| 2,918,404 | 12/1959 | Mende et al. | 128/271 |
| 2,943,979 | 7/1960 | Elias | 128/270 |
| 3,345,988 | 10/1967 | Vitello | 206/620 |
| 3,570,662 | 3/1971 | Polyak | 128/261 X |
| 3,608,566 | 9/1971 | Storandt | 128/272 UX |
| 3,768,725 | 10/1973 | Pilaro | 206/604 |
| 3,770,122 | 11/1973 | Thiele | 206/484 |
| 3,850,084 | 11/1974 | Fowler et al. | 206/306 |
| 3,950,158 | 4/1976 | Gossett | 206/219 |
| 3,967,728 | 7/1976 | Gordon | 206/364 |
| 4,007,838 | 2/1977 | Awad | 206/484 |

FOREIGN PATENT DOCUMENTS

| | | | |
|---|---|---|---|
| 6,614,822 | 4/1967 | Netherlands | 206/438 |
| 697,723 | 9/1953 | United Kingdom | 206/219 |
| 272,128 | 9/1970 | U.S.S.R. | 206/219 |

OTHER PUBLICATIONS

Bliss, A. R. *Vaginal Preparations*, In The Drug and Cosmetic Industry: pp. 50–51, Jul. 1937, 41.
Handbook of Nonprescription Drugs, 5th Edition, American Pharmaceutical Association, pp. 201–208, Jan. 1977.

*Primary Examiner*—Robert W. Michell
*Assistant Examiner*—Jerome D. Stremcha
*Attorney, Agent, or Firm*—Brown & Martin

[57] ABSTRACT

A contraceptive containing device including a contraceptive gel having a pH of less than 3.0; an elongated casing containing the gel and having an insertion end extending beyond the gel; and a hygienically sealed pouch enclosing the casing. The seal at one end of the pouch overlaps the insertion end of the casing to secure the casing to the pouch and close the insertion end of the casing. The casing is weakened in a region near where it is secured to the pouch for tearing when the pouch is opened to expose the casing and the casing is pulled with respect to the overlapping end of the pouch so as to provide a shearing stress in the casing near the insertion end, for thereby separating the casing from the pouch.

6 Claims, 6 Drawing Figures

CONTRACEPTIVE CONTAINING DEVICE

CROSS REFERENCE TO RELATED APPLICATION

This application is a continuation-in-part of a co-pending application entitled "Contraceptive Device", Ser. No. 732,800 filed Oct. 13, 1976, now U.S. Pat. No. 4,027,670.

BACKGROUND OF THE INVENTION

The present invention generally pertains to contraceptive devices and is particularly directed to contraceptive devices containing a contraceptive gel for insertion into the vagina.

In view of the rapidly expanding rate of growth of the world's population, there is a great need for improvement in contraceptive devices. The "pill" has proven unsatisfactory in many cases because of harmful side effects, as have intra-uterine devices. Other means of preventing conception, such as the "rhythm method" and the use of condoms, have not been reliable.

There is, however, a reliable and safe method of preventing conception. According to God's natural law, conception is impossible when the pH within the vagina is less than 4.0. Consistent with this law of nature, the Essenes over 2,000 years ago prescribed as a method of contraception the placement of a rose hip in the vagina during intercourse, the rose hip being rich in ascorbic acid and having the effect of lowering the pH within the vagina sufficiently to prevent conception. It is also known that a lemon slice may be inserted into the vagina before intercourse to lower the pH in order to prevent conception.

This method of contraception has not been widely accepted, however. The use of rose hips and lemon slices is neither practical nor convenient.

There has been one known contraceptive device based on this natural law. This device is a suppository type device containing a concentrated synthetic chemical formulation (such as boric acid, alum, thymol, monochlorothymol, phenyimercuric borate and aromatics, for example) for lowering the pH to less than 4.0. This formulation is carried by hardened cocoa butter in a bullet-shaped suppository and is spread within the vagina when the cocoa butter melts, a process requiring a wait of a few minutes after the suppository is inserted. This contraceptive device has not proven fully satisfactory in view of such a wait. Also, because of the nature of the synthetic chemical formulation, it can be applied in only a relatively small dosage of not more than about 3 grams, thus limiting the duration over which it is effective for preventing conception.

In the cross-referenced co-pending application of the present inventor there is described a contraceptive device containing a contraceptive gel for insertion into the vagina. The gel is made of natural harmless ingredients and has a pH of less than 3.0. The gel includes citric acid for lowering the pH in the vagina to less than 4.0; glycerine which acts as an emollient lubricant, and as an emulsifier; aromatic malic acid, which acts as a gel stabilizer and as an aromatic deodorant; kelco and/or wood cellulose, which keeps the gel from liquifying at high temperatures; and distilled water. The gel is reliable safe and inexpensive.

The contraceptive device described in said co-pending application includes a delicate elongated inside sausage casing containing the gel, and having a closed insertion end that will open to release the gel when the inside casing is squeezed; a lubricant covering the outside of the inside casing at the insertion end; a semi-sausage casing covering the lubricated insertion end of the inside casing for maintaining the lubricant in a lubricant state and at the insertion end, the semi-sauage casing having a closed end fitted over the lubricated insertion end of the inside casing and an open end fitted over the inside casing near the longitudinal mid-portion of the inside casing; and a tear strip having a first length removably attached to the open end of the semi-sausage casing and to the inside casing for hygenically sealing the lubricated insertion end of the inside casing and a second length attached to the semi-sausage casing to enable removal of the semi-sausage casing for exposing the lubricated insertion end of the inside sausage casing.

Although the contraceptive device described in said co-pending application is an inexpensive contraceptive device that can be used quickly in a convenient uncomplicated manner, it is the object of the present invention to provide an improved contraceptive device containing a contraceptive gel having a pH of less than 3.0 that is less complex and thereby even more inexpensive, so that it can be made available economically to more members to this world's burgeoning population.

SUMMARY OF THE INVENTION

The contraceptive containing device of the present invention includes a contraceptive gel having a pH of less than 3.0, an elongated casing containing the gel, and having an insertion end extending beyond the gel; and a hygenically sealed pouch enclosing the casing. The seal at the end of the pouch overlaps the insertion end of the casing to secure the casing to the pouch and close the insertion end of the casing.

Preferably the overlapping end of the pouch consists of sheetlike surfaces that are sealed together with the insertion end of the casing therebetween; and the pouch consists of a single sheet of material.

The casing is weakened in a region near where the casing is secured to the pouch for tearing when the pouch is opened to expose the casing and the casing is pulled with respect to the overlapping end of the pouch so as to provide a shearing stress in the casing for thereby separating the casing from the pouch. In one preferred embodiment the insertion end also is closed between the weakened region and the gel by a closure that will open to release the gel when the casing is squeezed after the casing has been separated from the pouch. In an alternative preferred embodiment, the insertion end is opened to enable release of the gel when the casing is separated from the pouch.

In a preferred embodiment of the contraceptive device according to the present invention wherein the pouch includes flat sealed surfaces at the sides of the pouch extending beyond the casing, a perforation is included in at least one side of the pouch other than at the overlapping end of the pouch for enabling the pouch to be torn open by the application of shear stress at the perforation.

BRIEF DESCRIPTION OF THE DRAWING

FIG. 7 is a top plan view of an alternative embodiment of the contraceptive device.

DESCRIPTION OF THE PREFERRED EMBODIMENTS

Figure 1:
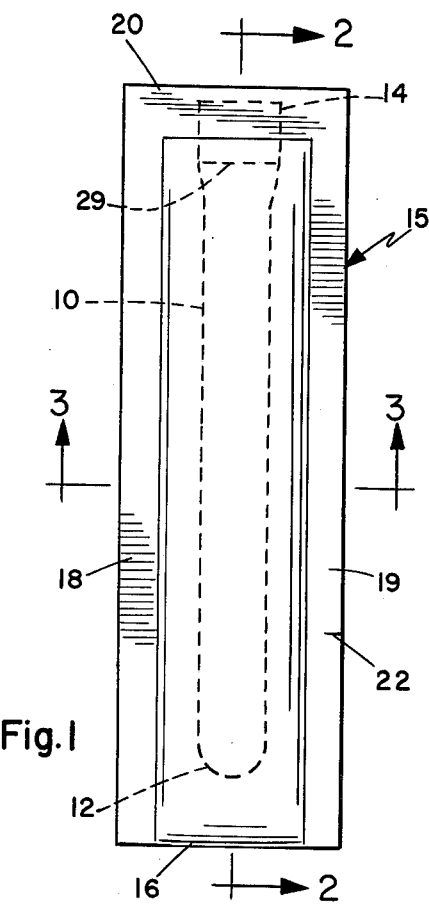
FIG. 1 is a top plan view of the contraceptive device of the present invention.

The contraceptive gel is manufactured from edible, natural, non-irritating, harmless ingredients that are biodegradable. In the preferred embodiment, the ingredients are mixed in the following approximate proportions: 90 percent distilled water; 2 percent citric acid; 5 percent glycerine; 1 percent aromatic malic acid and 2 percent kelco and/or wood cellulose. The citric acid is derived from lemons, the glycerine from coconut oil, the malic acid from apples, the kelco from ocean kelp or dulse, and the wool cellulose from wood pulp. A contraceptive gel of such proportions has a stable pH of less than 3.0. Some other edible acid, such as an aromatic acetic acid (which is red grape vinegar) may be substituted for the citric acid.

Referring to the drawing, the contraceptive gel is contained in an elongated casing 10. The size of the casing 10 is dependent upon the quantity of contraceptive gel 11 contained therein, with one-quarter ounce (7 grams), one-half ounce (14 grams) and one ounce (28 grams) size containers being preferred. The larger sizes provide longer lasting protection against conception. It has been determined that one ounce of gel having a pH of about 2.0 to 2.3 will maintain the pH within the vagina safely below 4.0 until after approximately 20 orgasms, or after the insertion of approximately 10 ounces of semen, which has an average pH of about 9.0 to 9.4. This degree of protection is significantly longer than with the prior art suppository type contraceptive which is limited to relatively smaller insertion dosages because of the nature of its synthetic chemical formulation, which in large amounts would become irritating.

The casing 10 is tubular shaped and has a closed end 12 that is rounded. The opposite end 14 of the casing 10 is an insertion end 14, which is inserted into the vagina for dispensing the contraceptive gel. The insertion end 14 extends beyond the gel 11 in the casing 10 by approximately one-half inch (1.3 cm). The diameter of the casing 10 is about one-half inch (1.3 cm) or less, so that the casing need not be lubricated for insertion into the vagina.

The casing 10 is an inexpensive wax paper or a plastic material.

The casing 10 is enclosed by a pouch 15. The pouch 15 is constructed of a single sheet of material which is folded at one end 16. The flat surfaces of the folded sheet extend beyond the casing 10 by approximately one-sixteenth inch (1.6 mm) to one-half inch (1.3 cm) on the remaining three sides 18, 19, 20 of the pouch 15 to enable easy separation. The flat surfaces of the sheet at the three sides 18, 19, and 20 are heat sealed together. Alternatively the pouch may be constructed of two matching sheets that are heat sealed together at all four sides.

The tip of the insertion end 14 of the casing 10 is positioned between the sheetlike surfaces of the pouch 15 at one end 20 of the pouch 15 that overlaps the insertion 14, whereupon the casing 10 is secured to the pouch 15 when the sheetlike surfaces at the overlapping end 20 of the pouch 15 are heat sealed together.

The sheet material of the pouch includes plastic, metal foil or wax paper, with the least expensive material consistent with the storage specifications for the gel 11 being preferred.

Figure 4:
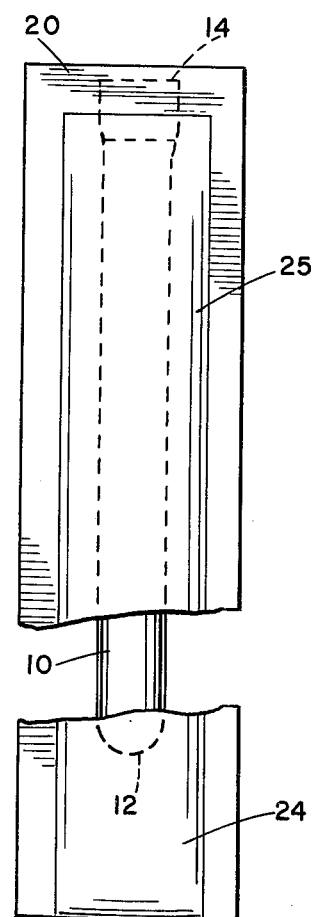
FIG. 4 is a view similar to FIG. 1, but showing separation of the pouch.
Figure 3:
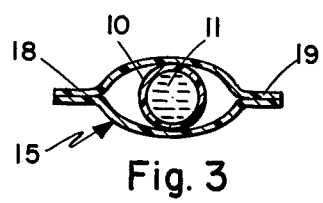
FIG. 3 is a sectional view taken on line 3—3 of FIG. 1.
Figure 5:
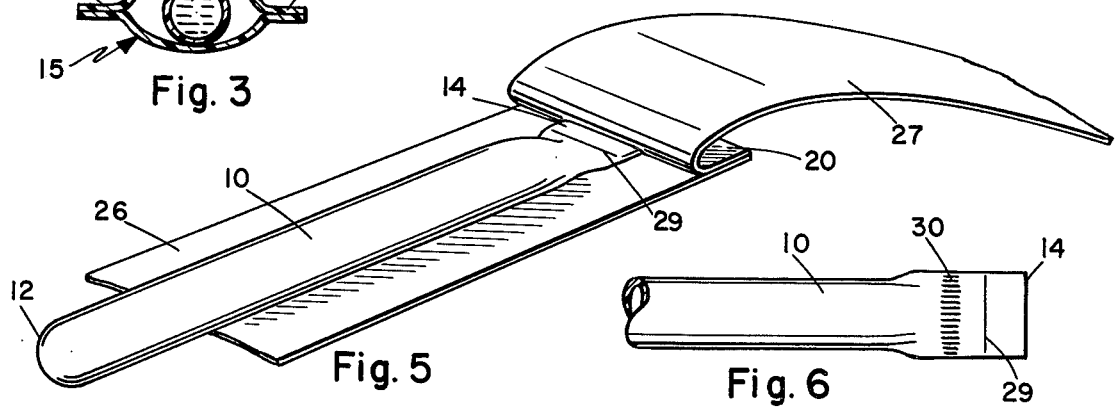
FIG. 5 is a perspective view showing the pouch opened to expose the inner casing.

One side 19 of the pouch 15 includes a perforation 22 for enabling the pouch to be torn open by the application of shear stress at the perforation 22. After the pouch 15 is torn open the bottom portion 24 of the pouch 15 is separated from the top portion 25 of the pouch 15. (See FIG. 4) The broad surfaces 26 and 27 of the top portion 25 are pulled apart (as shown in FIG. 5) to expose the casing 10 extending from the overlapping end 20 of the pouch 15.

The casing 10 is weakened in a region 29 near where the casing 10 is secured to the pouch 15 for tearing when the pouch 15 is opened to expose the casing 10 and the casing 10 is pulled with respect to the overlapping end 20 of the pouch 15 so as to provide a shearing stress in the casing 10 near the insertion end 14, for thereby separating the casing 10 from the pouch 15.

Figure 6:
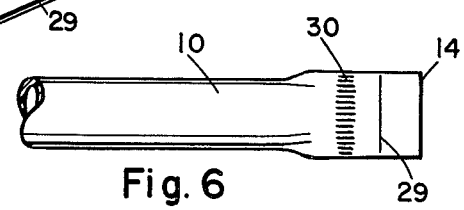
FIG. 6 illustrates an alternative end seal for the gel casing.

In one preferred embodiment (FIG. 6), the insertion end 14 of the casing 10 is also closed between the weakened region 29 and the gel 11 by a closure 30 that will open to release the gel 11 when the casing 10 is squeezed after the casing 10 has been separated from the pouch 15.

Figure 2:
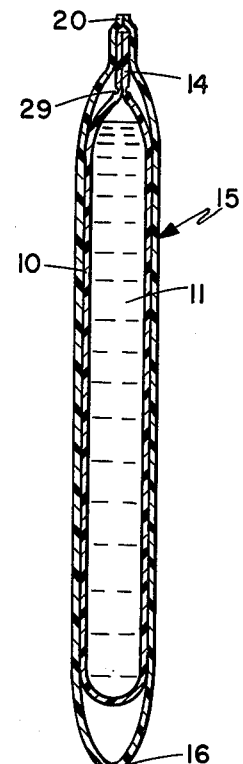
FIG. 2 is a sectional view taken on line 2—2 of FIG. 1.

In an alternative preferred embodiment (FIG. 2), the insertion end 14 is opened to enable release of the gel 11 when the casing 10 is separated from the pouch 15.

Having described my invention, I now claim:

1. A contraceptive containing device, comprising a contraceptive gel having a pH less than 3.0;
    an elongated casing containing the gel, and having an insertion end extending beyond the gel wherein said insertion end has an outer portion, and an inner portion between said outer portion and said gel; and
    a hygienically sealed pouch enclosing the casing and having a seal at one end of the pouch which overlaps said outer portion of the insertion end of the casing to secure the casing to the pouch and close the insertion end of the casing; wherein said casing has a weakened region in said inner portion of the insertion end, whereby the casing can be exposed by the application of shear stress at a region in at least one side of the pouch excluding the pouch portion which overlaps the insertion end of the casing to allow removal of a portion of the pouch, and wherein said casing can be removed from the remaining portion of the pouch by pulling on the end of the casing remote from the insertion end to provide a shearing stress in the casing near the insertion end of the pouch for causing said casing to detach from said remaining portion of the pouch.

2. A contraceptive device according to claim 1, wherein the pouch consists of sheet-like surfaces.

3. A contraceptive device according to claim 1, wherein the pouch consists of a single sheet of material.

4. A contraceptive device according to claim 1, further comprising
    closure means for closing the casing between the weakened region and by gel, wherein the closure means is adapted for opening to release the gel when the casing is squeezed after the casing has been separated from the pouch.

5. A contraceptive device according to claim 1 wherein the insertion end of the casing is adapted for opening to enable release of the gel when the casing is separated.

6. A contraceptive device according to claim 1, wherein the pouch includes flat sealed surfaces at the sides of the pouch extending beyond the casing, and wherein at least one side of the pouch excluding the pouch portion which overlaps the insertion end of the casing includes a perforation.

* * * * *